US008118735B2

(12) United States Patent
Voegele (10) Patent No.: US 8,118,735 B2
(45) Date of Patent: Feb. 21, 2012

(54) ROTATIONAL CONTROL FOR A HAND ASSISTED LAPAROSCOPIC SEAL ASSEMBLY

(75) Inventor: James W. Voegele, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1182 days.

(21) Appl. No.: 11/902,945

(22) Filed: Sep. 26, 2007

(65) Prior Publication Data

US 2009/0082632 A1 Mar. 26, 2009

Related U.S. Application Data

(63) Continuation-in-part of application No. 11/399,145, filed on Apr. 5, 2006, now abandoned.

(60) Provisional application No. 60/669,514, filed on Apr. 8, 2005, provisional application No. 60/700,176, filed on Jul. 18, 2005.

(51) Int. Cl.
*A61B 1/00* (2006.01)
(52) U.S. Cl. ...................................................... 600/184
(58) Field of Classification Search ................... 600/184, 600/201, 206, 208, 215, 233
See application file for complete search history.

(56) References Cited

U.S. PATENT DOCUMENTS

| 4,094,492 A | 6/1978 | Beeman et al. |
|---|---|---|
| 5,449,141 A | 9/1995 | Gillett et al. |
| 5,640,977 A | 6/1997 | Leahy et al. |
| 6,077,288 A | 6/2000 | Shimomura et al. |
| 6,589,167 B1 | 7/2003 | Shimomura et al. |
| 7,300,399 B2 | 11/2007 | Bonadio et al. |
| 7,393,322 B2 | 7/2008 | Wenchell |
| 7,678,046 B2 | 3/2010 | White et al. |
| 7,749,161 B2 | 7/2010 | Beckman et al. |
| 7,766,822 B2 | 8/2010 | White et al. |
| 2004/0154624 A1 * | 8/2004 | Bonadio et al. ............... 128/849 |
| 2005/0155611 A1 | 7/2005 | Vaugh et al. |
| 2006/0149306 A1 | 7/2006 | Hart et al. |
| 2006/0247678 A1 * | 11/2006 | Weisenburgh et al. ....... 606/205 |
| 2008/0146884 A1 | 6/2008 | Beckman et al. |
| 2008/0208175 A1 | 8/2008 | Beckman et al. |
| 2008/0208222 A1 | 8/2008 | Beckman et al. |

FOREIGN PATENT DOCUMENTS

WO WO2004/054456 7/2004
* cited by examiner

*Primary Examiner* — Ryan Severson
(74) *Attorney, Agent, or Firm* — Welsh Flaxman & Gitler LLC (57) ABSTRACT

A seal assembly for permitting hand assisted laparoscopic procedures includes a seal cap having a seal positioned within a housing. The housing includes a lower seal ring having a track which supports an upper seal ring for relative rotational motion, wherein the seal is supported between the upper seal ring and the lower seal ring for rotation between an open orientation and a closed orientation. The upper seal ring includes a first ring member and a second ring member oriented for movement relative thereto, wherein a latching mechanism is positioned between the first ring member and the second ring member for selectively controlling movement of the first ring member relative to the second ring member. The seal assembly also includes a rotational control mechanism controlling motion of the upper seal ring relative to the lower seal ring.

20 Claims, 8 Drawing Sheets

ROTATIONAL CONTROL FOR A HAND ASSISTED LAPAROSCOPIC SEAL ASSEMBLY

CROSS REFERENCE TO RELATED APPLICATIONS

This application is a continuation-in-part of U.S. patent application Ser. No. 11/399,145, entitled "SURGICAL INSTRUMENT SYSTEM", filed Apr. 5, 2006, which is now abandoned, which claims the benefit of U.S. Provisional Patent Application Ser. Nos. 60/669,514, filed Apr. 8, 2005, and 60/700,176, filed Jul. 18, 2005.

BACKGROUND OF THE INVENTION

1. Field of the Invention

The invention relates to laparoscopic devices. In particular, the invention relates to a laparoscopic seal assembly having a release mechanism permitting unrestricted opening of the seal assembly.

2. Description of the Related Art

In a minimally invasive, laparoscopic surgical procedure, a surgeon may place a number of small ports into the abdomen to gain access into the abdominal cavity of the patient. A surgeon may use, for example, a port for insufflating the abdominal cavity to create space, a port for introducing a laparoscope for viewing, and a number of other ports for introducing surgical instruments for operating on tissue. The benefits of minimally invasive procedures compared to open surgery procedures for treating certain types of wounds and diseases are now well known to include faster recovery time and less pain for the patient, better outcomes and lower overall costs.

In traditional, open surgery, surgeons may use their hands, together with the surgical instruments to manipulate tissues, to perform particular steps of the procedure and to obtain tactile feedback through their fingertips to verify the nature of particular tissues. Also in open surgery, the size and shape of the instrument that a surgeon may place into the abdominal cavity, as well as the size and shape of tissues that a surgeon may remove, obviously is not nearly as limited as in laparoscopic surgery.

Hand assisted, laparoscopic surgery (HALS) combines some of the benefits of both the open and the laparoscopic methods. In a hand assisted laparoscopic surgical procedure, a surgeon still places small ports into the abdomen to insufflate, to view and to introduce instruments into the abdominal cavity. In a HALS procedure, a surgeon also creates an incision into the abdominal wall large enough to accommodate the surgeon's hand. The incision may be retracted and draped to provide a suitably sized and protected opening. A surgeon may also place a laparoscopic access device, also referred to as a laparoscopic seal assembly (or hand access seal assembly, hand access device, HALS seal assembly or HALS access device), into the incision to maintain insufflation in the abdominal cavity while the surgeon's hand is either inserted into the cavity through the laparoscopic seal assembly or removed from the cavity. The advent of HALS and the laparoscopic seal assembly creates numerous opportunities for creating and improving surgical devices and methods.

SUMMARY OF THE INVENTION

It is, therefore, an object of the present invention to provide a seal assembly for permitting hand assisted laparoscopic procedures. The seal assembly includes a seal cap having a seal positioned within a housing. The housing includes a lower seal ring having a track which supports an upper seal ring for relative rotational motion, wherein the seal is supported between the upper seal ring and the lower seal ring for rotation between an open orientation and a closed orientation. The upper seal ring includes a first ring member and a second ring member oriented for movement relative thereto, wherein a latching mechanism is positioned between the first ring member and the second ring member for selectively controlling movement of the first ring member relative to the second ring member. The seal assembly also includes a rotational control mechanism controlling motion of the upper seal ring relative to the lower seal ring.

It is also an object of the present invention to provide a seal assembly wherein the rotational control mechanism is positioned between the second ring member and the lower seal ring.

It is also another object of the present invention to provide a seal assembly wherein the rotational control mechanism is a ratchet rotational control mechanism.

It is also a further object of the present invention to provide a seal assembly wherein the rotational control mechanism is positioned between the second ring member and the lower seal ring.

It is still a further object of the present invention to provide a seal assembly wherein the ratchet rotational control mechanism includes a ratchet arm oriented to engage a ratchet surface.

It is yet another object of the present invention to provide a seal assembly wherein the ratchet arm is coupled to the upper seal ring and the ratchet surface is coupled to the lower seal ring.

It is also an object of the present invention to provide a seal assembly wherein the ratchet arm is coupled to the second ring member of the upper seal ring.

It is another object of the present invention to provide a seal assembly including first and second ratchet surfaces on the lower seal ring.

It is still another object of the present invention to provide a seal assembly wherein the seal is an iris seal.

It is yet another object of the present invention to provide a seal assembly including a spring biasing the upper seal ring relative to the lower seal ring.

It is also an object of the present invention to provide a seal assembly wherein an upper end of the seal is connected to the upper seal ring and a lower end of the seal is connected to the lower seal ring.

It is also a further object of the present invention to provide a seal assembly including an ergonomic cover member secured to the upper seal ring, wherein the ergonomic cover member includes a contoured outer surface providing for improved handling and twisting of the upper seal ring for opening and closing the seal.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for teaching one skilled in the art how to make and/or use the invention.

Referring to FIGS. 1 to 13, a seal assembly 10 for permitting hand assisted laparoscopic procedures is disclosed. As will be discussed below in greater detail, the present seal assembly 10 provides a mechanism for overriding the need to counter-rotate the iris-tightening ring, that is, the upper seal ring 72, to disengage the locking feature. As will be discussed below in greater detail, this employs the incorporation of first and second ring members in the construction of the upper seal ring 72 such that the iris seal 12 may be freely rotated without actuation of the locking feature.

As those skilled in the art will certainly appreciate, laparoscopic seal assemblies are commonly employed during laparoscopic procedures and may take a variety of forms. For example, and in accordance with a preferred embodiment, a laparoscopic seal assembly as disclosed in commonly owned U.S. patent application Ser. No. 11/714,267, entitled "HAND ASSISTED LAPAROSCOPIC SEAL ASSEMBLY WITH A RATCHET MECHANISM", filed Mar. 6, 2007, is incorporated herein by reference.

In accordance with a preferred embodiment, the seal assembly 10 generally employs an iris seal cap 14 and retractor 18 to ensure abdominal pressure is not compromised during hand exchanges while hand assisted laparoscopic procedures are performed. As such, and in accordance with a preferred embodiment of the present invention, the seal assembly 10 includes an iris seal 12 housed within a seal cap 14. The iris seal 12 includes a central access opening 86 allowing access to the body cavity as desired by the surgeon, or other medical practitioner, performing the procedure. As a result the iris seal 12 is shaped and dimensioned to create a gas tight barrier around the surgeon's wrist when inserted through the seal assembly 10 and also creates a gas tight barrier between the interior abdominal space and the external environment when a hand is not inserted through the seal assembly 10. As will be discussed below in greater detail, adjustment of the iris seal 12, and ultimately the access opening 86, provides for access to the body cavity in this highly controlled manner.

Referring to the various figures, the seal cap 14 includes an iris seal 12 positioned within a housing 16. The housing 16 is made of soft textured material such as the thermoplastic elastomer SANTOPRENE, or other like materials, and supports the iris seal 12 in a concentric manner. Although SANTOPRENE is disclosed in accordance with a preferred embodiment, other housing materials may be used without departing from the spirit of the present invention.

As with prior hand assisted laparoscopic seal assemblies, the housing 16 of the present seal assembly 10 is secured to the abdominal wall 20 of an individual patient by first creating an incision and positioning the retractor 18 above the incision. Thereafter, the retractor 18, which will eventually be coupled to the seal cap 14, is inserted into the body cavity with the abdominal wall 20 therebetween. The seal cap 14 is then connected to the retractor 18 in a manner securely connecting and supporting the seal cap 14 on the outside of the abdominal wall 20 with the abdominal wall 20 resiliently held between the seal cap 14 and the retractor 18.

More particularly, the surgical site is prepared in accordance with conventional standard hospital procedures, making sure the skin is clean and dry. Thereafter, a template is placed over the incision site and an incision line is marked upon the template using a sterile skin marker. As those skilled in the art will appreciate, the glove size dictates the size of the incision. For example, if the surgeon's glove size is 7, a 6.5 to 7.0 cm incision is usually appropriate. Thereafter, an incision is made along the marked incision line. The incision size is thereafter verified by inserting the surgeon's hand into the abdomen prior to installing the retractor 18 and the present seal cap 14. If the incision is too small, the incision is extended on each end as required to maintain the central position of the incision relative to the placement of the present seal assembly 10. Thereafter, the back band 22 of the retractor 18 is inserted through the incision. Using one's fingers, the retractor 18 is seated evenly under the peritoneum and the area is swept to ensure the retractor 18 is not lying between tissue layers. Thereafter, the seal cap 14 is attached to the retractor 18 via an attachment ring 24, which may be rigid but is not limited to such construction, and adjustments are made to ensure the seal assembly 10 is secured with the patient's abdomen maintaining pneumo. As those skilled in the art will certainly appreciate, the retractor may be a fixed length or adjustable length retractor. In either case, the retractor 18 must fit the abdominal wall 20 thickness to maintain stability and pneumo. As briefly discussed above, the present seal assembly 10 is provided with an attachment ring 24, which ultimately forms part of the housing 16 of the seal cap 14 when it is secured thereto in the manner discussed below in greater detail, that is detachable from the remaining portions of the housing 16 for permitting selective attachment of the retractor 18 to the present seal cap 14. It is further contemplated the attachment ring 24 allows removal of the seal cap described herein which can be replaced with other accessory cap attachments, such as an instrument port cap.

Figure 1:
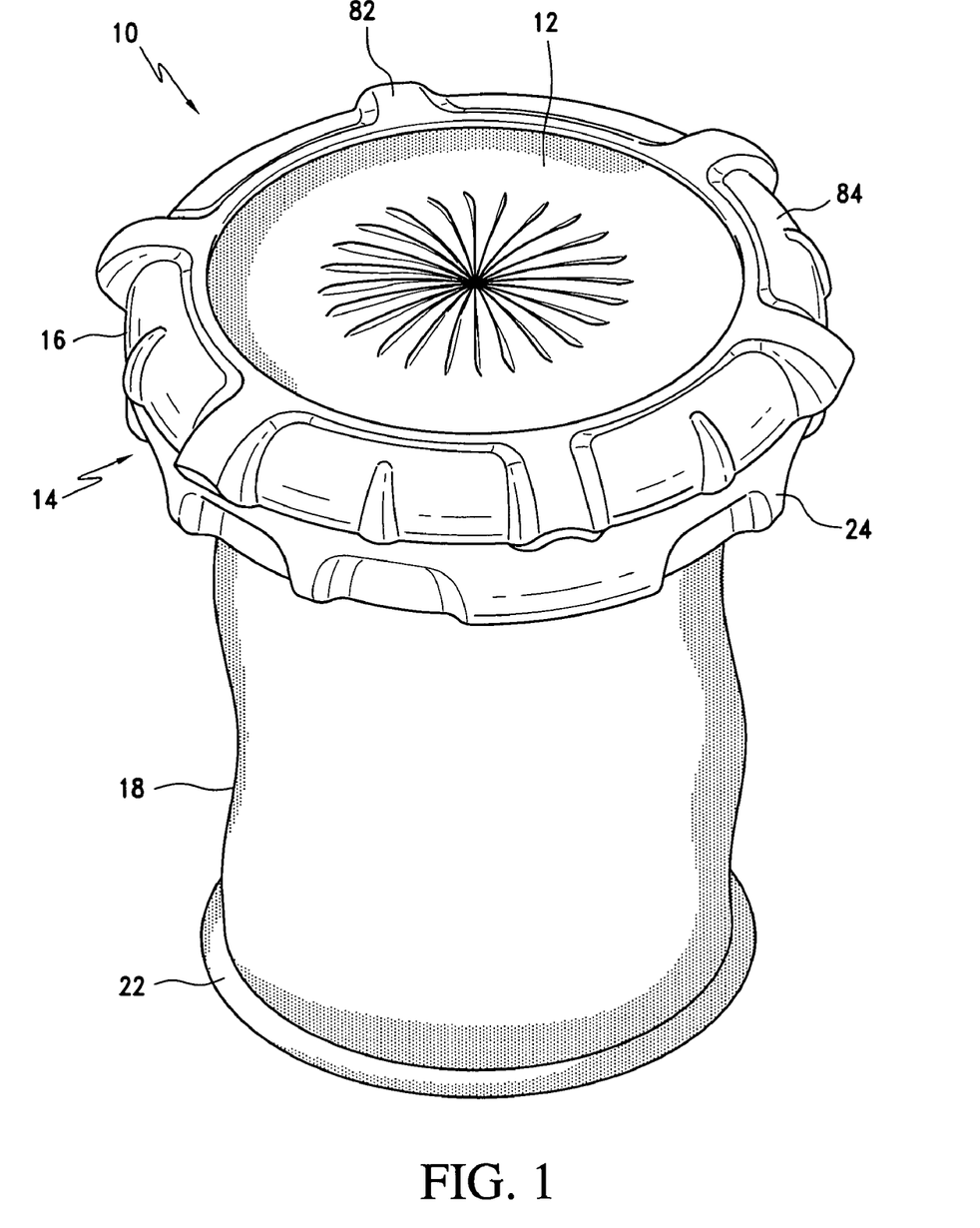
FIG. 1 is a perspective view of the present hand assisted laparoscopic seal assembly.
Figure 2:
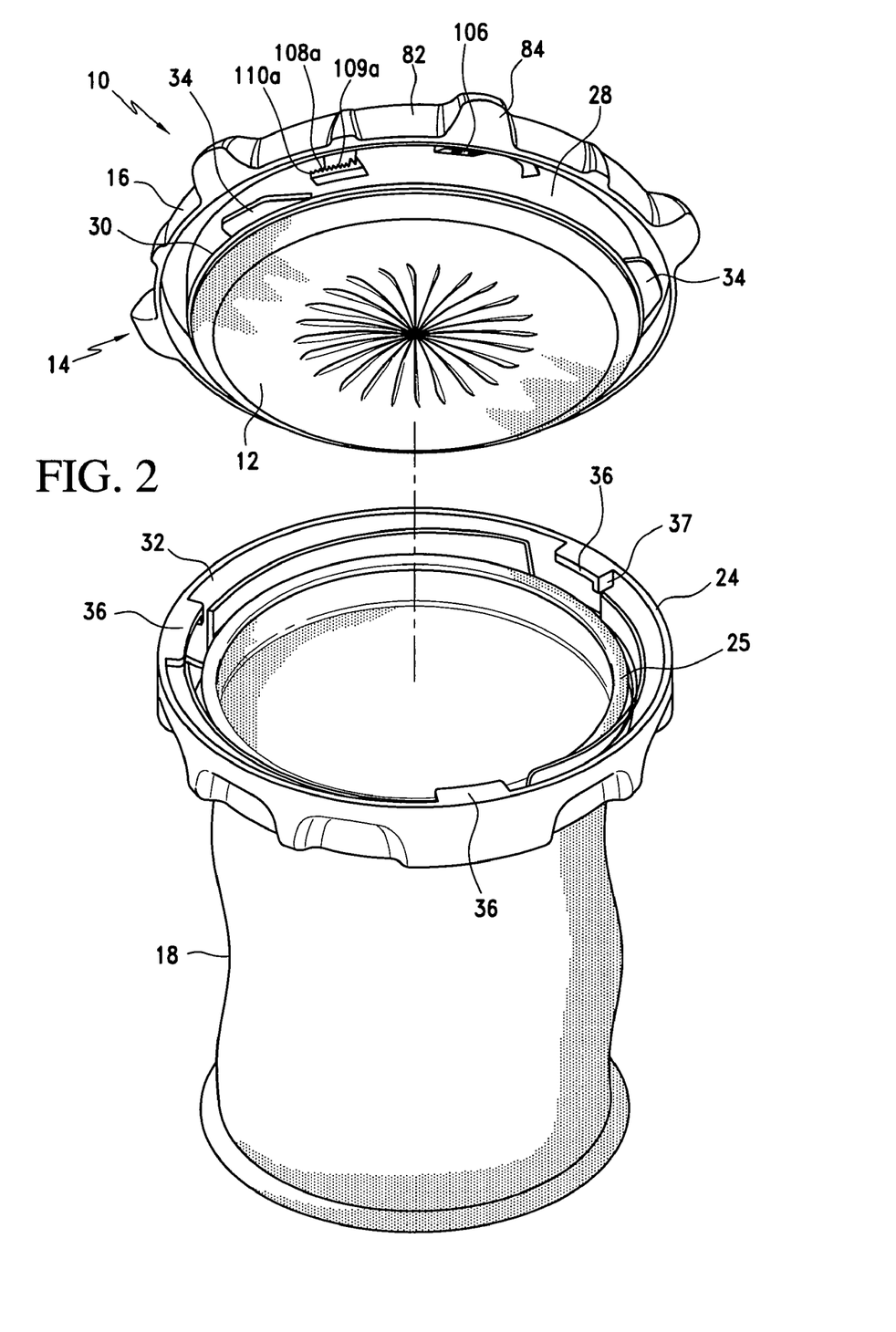
FIG. 2 is a perspective view of the hand assisted laparoscopic seal assembly with the attachment ring and retractor disengaged from the seal cap.
Figure 3:
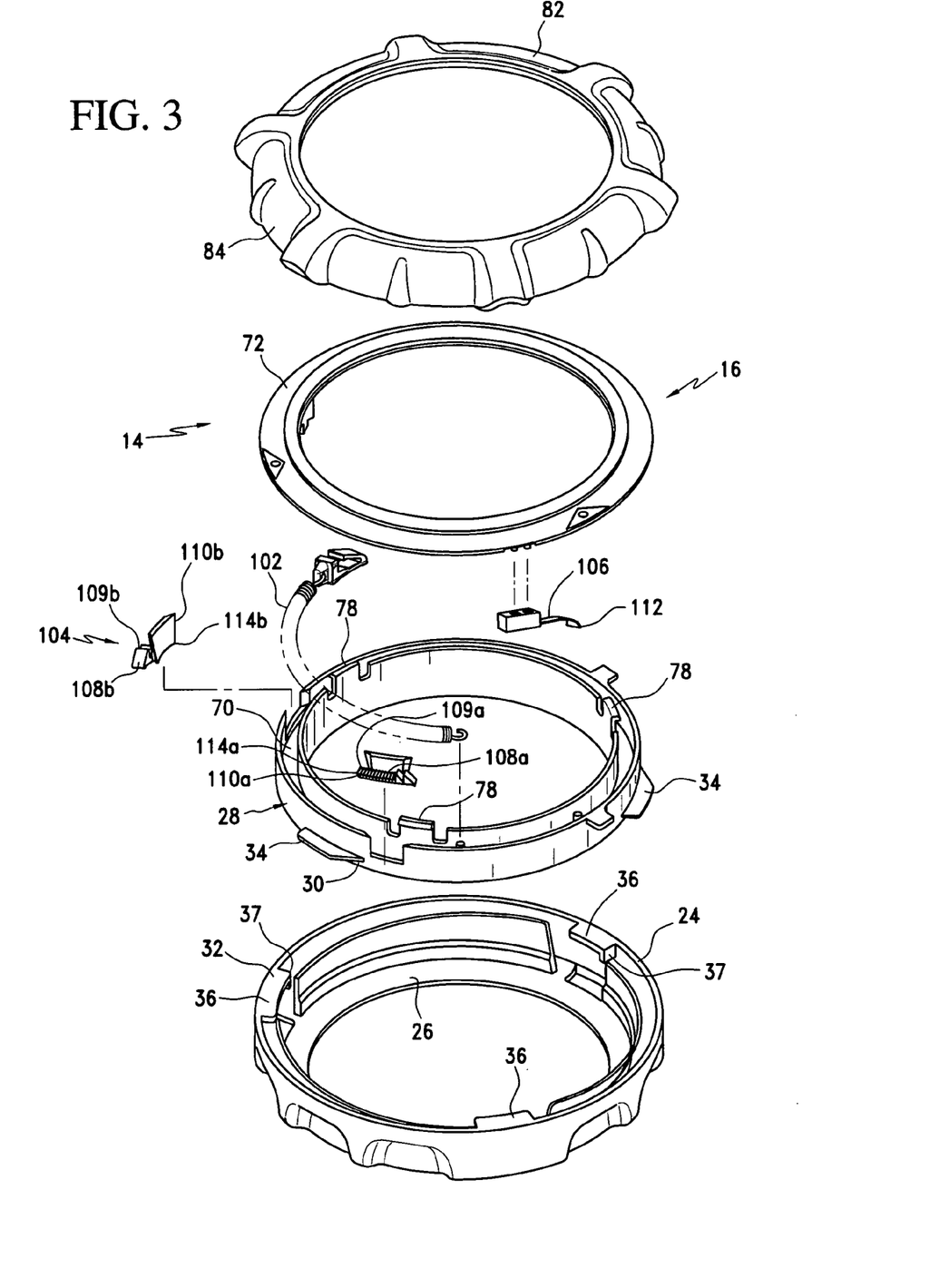
FIG. 3 is an exploded view of the seal cap of the present seal assembly.
Figure 4:
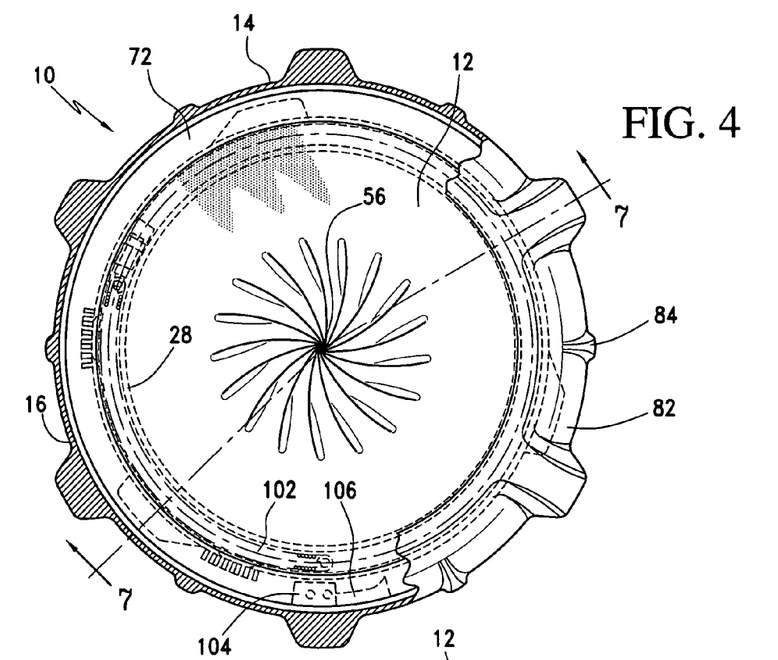
FIGS. 4, 5 and 6 are partial sectional top views showing actuation of the present hand assisted laparoscopic seal assembly respectively between a closed position, a partially opened orientation for hand insertion and a fully opened orientation for viewing and insertion of larger instruments.

In particular, the upper end 25 of the retractor 18 is seated upon a ledge 26 formed in the attachment ring 24 (best seen in FIGS. 2 and 3). Thereafter, the attachment ring 24 is secured to the remainder of the housing 16 such that the retractor 18 is securely positioned between the attachment ring 24 and a lower seal ring 28 of the seal cap 14.

Selective attachment and detachment of the attachment ring 24 from the lower seal ring 28 is achieved through the provision of interlocking engagement structures formed along the lower surface 30 of the lower seal ring 28 and the upper surface 32 of the attachment ring 24. In particular, the lower seal ring 28 is formed with a plurality of outwardly extending flanges 34 that are shaped and dimensioned for seating within inwardly facing recesses 36 formed along the attachment ring 24. As such, one need only place the lower seal ring 28 within the space defined by the attachment ring 24 and subsequently twist the outwardly extending flanges 34 into the inwardly extending recesses 36 to securely couple the attachment ring 24 to the lower seal ring 28, and ultimately to the remainder of the housing 16 of the seal cap 14. Rotation of the lower seal ring 28 relative to the attachment ring 24 is controlled by providing the recesses 36 with a transverse wall 37 that stops rotation of the lower seal ring 28 relative to the attachment ring 24. The wall 37 is positioned on the side of the recess 36 that is in the same rotational direction as the direction to open the iris seal 12 (and in accordance with a preferred embodiment, clockwise). When it is desired to detach the attachment ring 24 from the lower seal ring 28, one need only turn the lower seal ring 28 in the opposite direction, that is, counter-clockwise in accordance with a preferred embodiment, with slight pressure to overcome the frictional interference between the outwardly extending flanges 34 of the lower seal ring 28 and the inwardly directed recesses 36 of the attachment ring 24 such that the flanges 34 and recesses 36 are unseated in a manner permitting separation of the attachment ring 24 and the lower seal ring 28. It will be understood by those skilled in the art that the disconnect torque must be greater than the rotational torque of the iris seal 12.

Various other mechanisms for selective attachment of the attachment ring are disclosed in commonly owned U.S. patent application Ser. No. 11/730,922, entitled "HAND ASSISTED LAPAROSCOPIC SEAL ASSEMBLY WITH DETACHABLE ATTACHMENT RING", filed Apr. 4, 2007, which is incorporated herein by reference.

With regard to the upper end 25 of the retractor 14, it is preferably as disclosed in commonly owned U.S. patent application Ser. No. 11/458,325, filed Jul. 18, 2006, entitled "ROLL-UP WOUND PROTECTOR WITH TRICUSPIDATE RING", Ser. No. 11/458,328, filed Jul. 18, 2006, entitled "ROLL-UP WOUND PROTECTOR WITH ASYMMETRIC RING", and Ser. No. 11/458,329, filed Jul. 18, 2006, entitled "ROLL-UP WOUND PROTECTOR", which are incorporated herein by reference.

In accordance with a preferred embodiment, the iris seal 12 is a rotatable seal which selectively opens to permit passage of a surgeon's hand therethrough and automatically closes in a manner creating a gas tight barrier between the interior abdominal space and the external environment whether or not a hand or instrument 68 is inserted through the seal assembly 10. In particular, the housing 16 in which the iris seal 12 is supported includes a lower seal ring 28 having a track 70 which supports an upper seal ring 72 for relative rotational motion in a manner discussed below in greater detail.

As will be discussed below in greater detail, the upper end 74 of the iris seal 12 is permanently connected to the upper seal ring 72. The lower end 76 of the iris seal 12 is permanently connected to the lower seal ring 28. The upper seal ring 72 and the lower seal ring 28 are connected together for relative rotational movement in a manner allowing for opening and closing of the iris seal 12. In accordance with a preferred embodiment, the upper seal ring 72 and the lower seal ring 28 are connected by at least three snap tabs 78 located on the lower seal ring 28 that are shaped and dimensioned to engage a recess 80 along the inner edge of the upper seal ring 72.

An ergonomic cover member 82 is secured to the upper seal ring 72. The ergonomic cover member 82 includes a contoured outer surface 84 providing for improved handling and twisting of the upper seal ring 72 for opening and closing the iris seal 12 in accordance with the present invention. In accordance with a preferred embodiment, the ergonomic cover member 82 is a separate component fixedly secured to upper seal ring 72 such that rotational force applied to the ergonomic cover member 82 is transmitted on to the upper seal ring 72 for opening and closing of the iris seal 12. However, and as those skilled in the art will certainly appreciate, the ergonomic cover member 82 could be integrally formed with the upper seal ring 72, while still remaining within the spirit of the present invention.

Referring to FIGS. 4, 5, 6, 7 and 8, as discussed below in greater detail, the iris seal 12 is secured between the upper seal ring 72 and the lower seal ring 28. The upper seal ring 72 is supported within a track 70 of the lower seal ring 28 in a manner facilitating rotational movement between the upper seal ring 72 and the lower seal ring 28. In this way, the rotational movement of the upper seal ring 72 relative to the lower seal ring 28 is utilized to control the opening and closing of the iris seal 12 for one-hand insertion of a hand through the present seal assembly 10.

The iris seal 12 is mounted between the upper seal ring 72 and the lower seal ring 28 such that upon rotation of the upper seal ring 72 in a predetermined direction, the central access opening 86 of the iris seal 12 will open, providing a surgeon with an access opening 86 for passage of his or her hand therethrough. Automatically the upper seal ring 72, and ultimately, the iris seal 12 will rotate in the reverse direction, the access opening 86 will close securely about the wrist of the surgeon or instrument. That is, the upper seal ring 72 and the iris seal 12 are moved between open orientations (see FIGS. 5, 6 and 8) in which an access opening 86 is created within the iris seal 12 and a closed orientation (see FIGS. 4 and 7) in which the iris seal 12 is either wrapped about the wrist of a user with his or her hand inserted therein or substantially fully closed.

Opening and closing of the iris seal 12 is achieved by constructing the iris seal 12 in a folded configuration spanning the upper seal ring 72 and the lower seal ring 28 in a substantially taut configuration. As such, rotation of the upper seal ring 72 in a first direction will result in an increase of tension along the iris seal 12 in a manner drawing the fold outwardly, opening the central access opening 86 in the iris seal 12.

Figure 7:
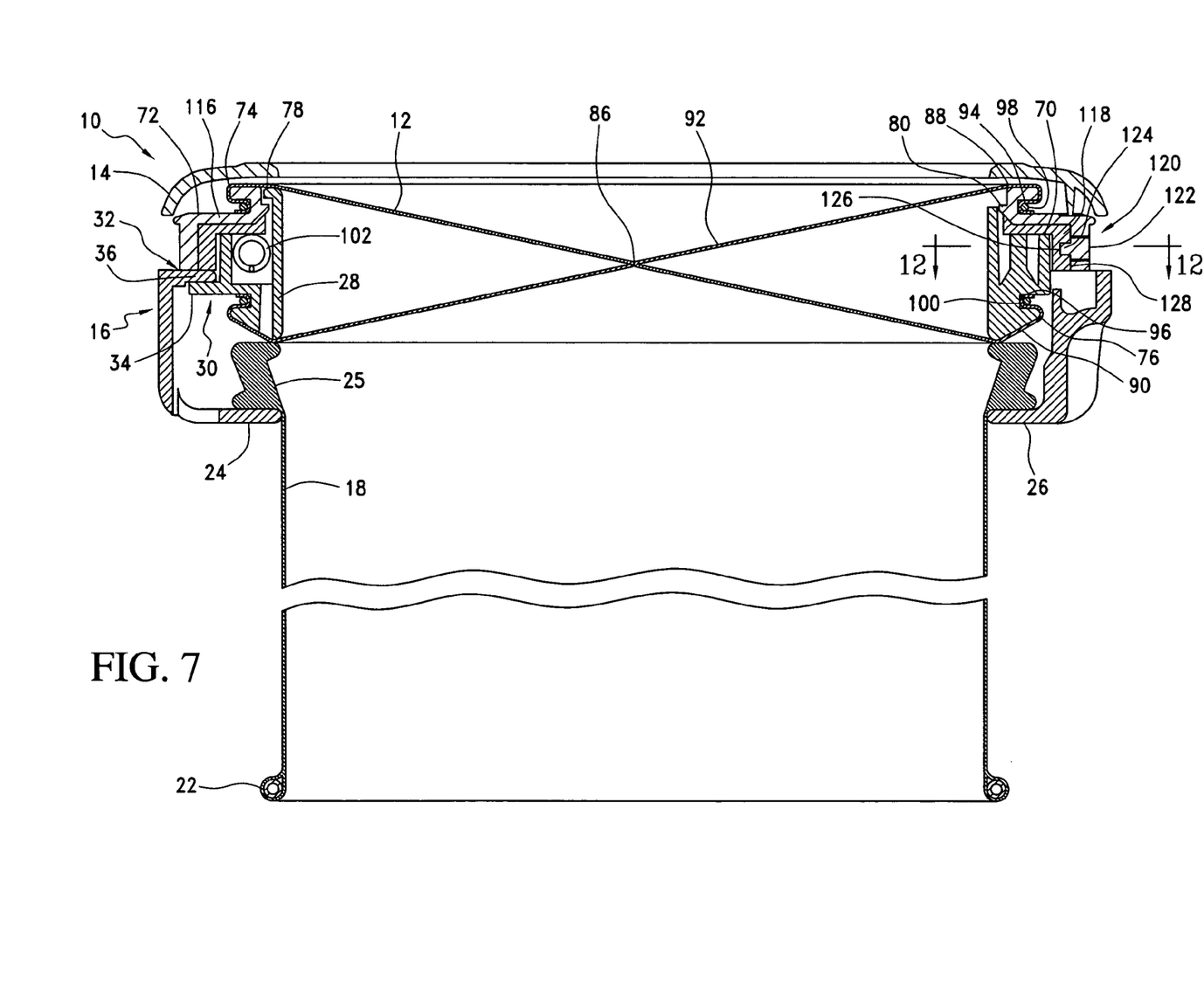
FIG. 7 is a cross sectional view taken along the line 7-7 in FIG. 4.
Figure 8:
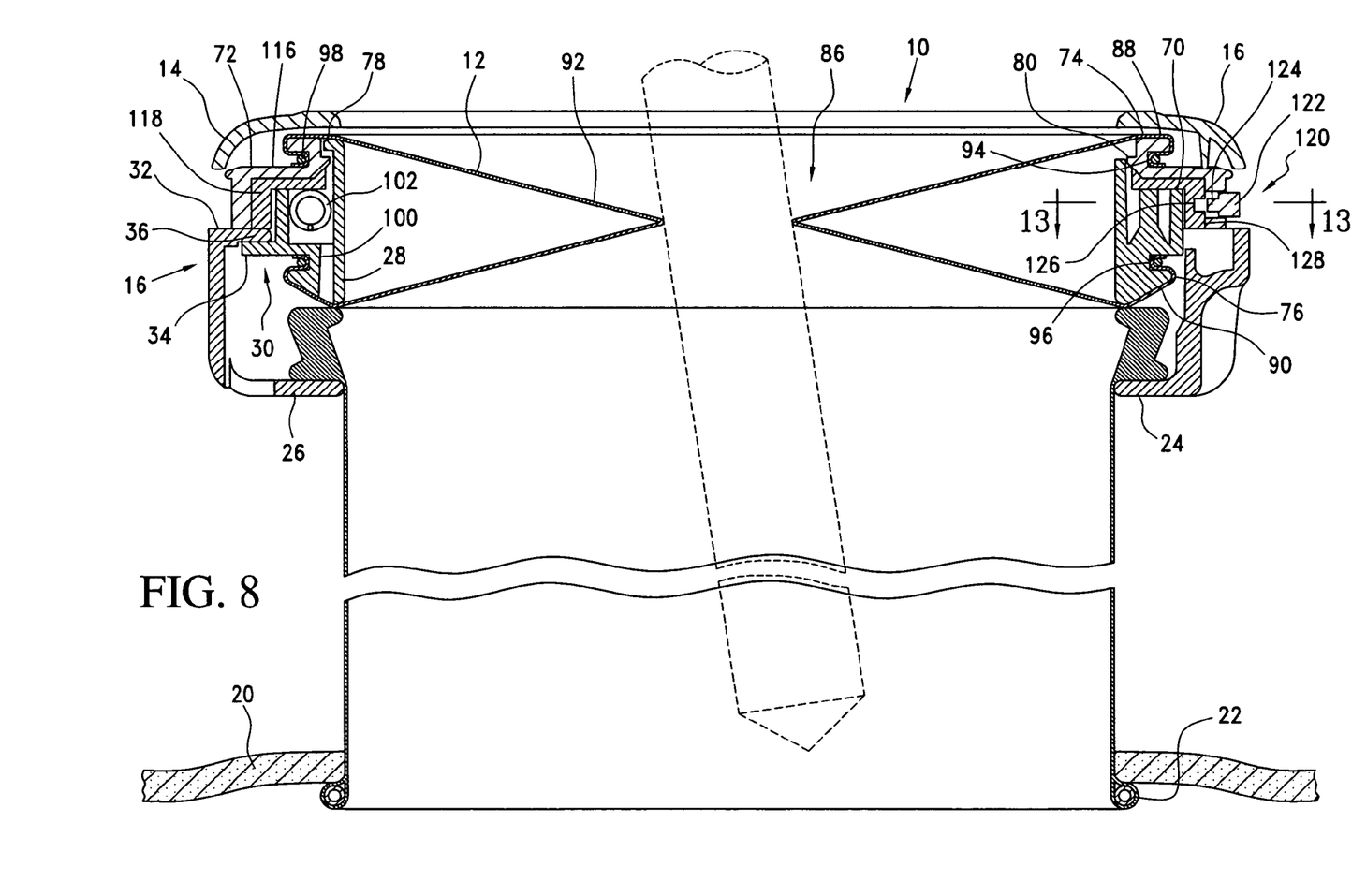
FIG. 8 is a cross sectional view taken along the line 8-8 in FIG. 6 with an instrument shown in phantom.
Figure 9:
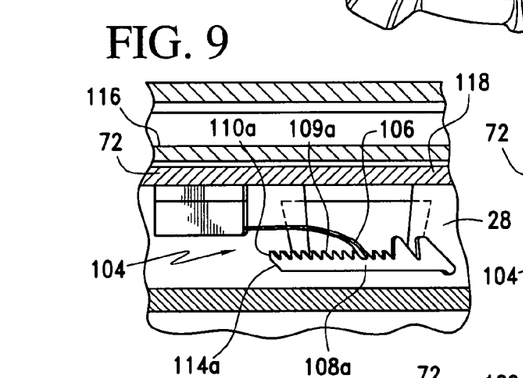
FIGS. 9, and 10 are detailed views of the ratchet mechanism in accordance with the present invention.
Figure 10:
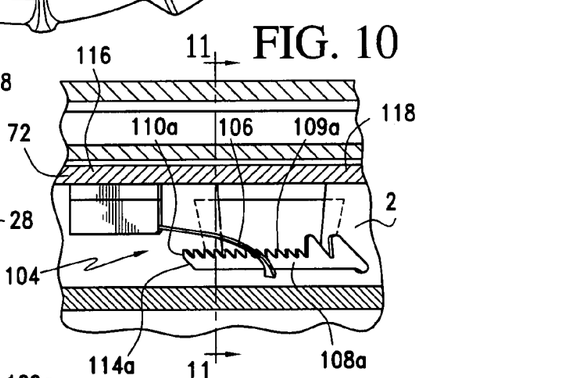
Figure 11:
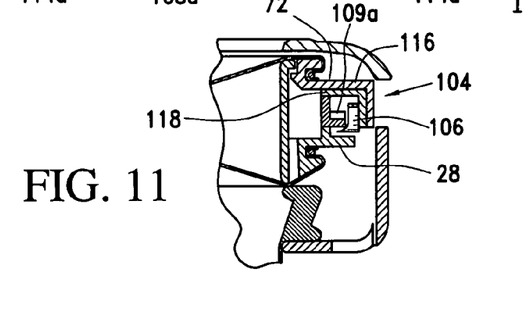
FIG. 11 is a cross sectional view along the line 11-11 in FIG. 10.
Figure 12:
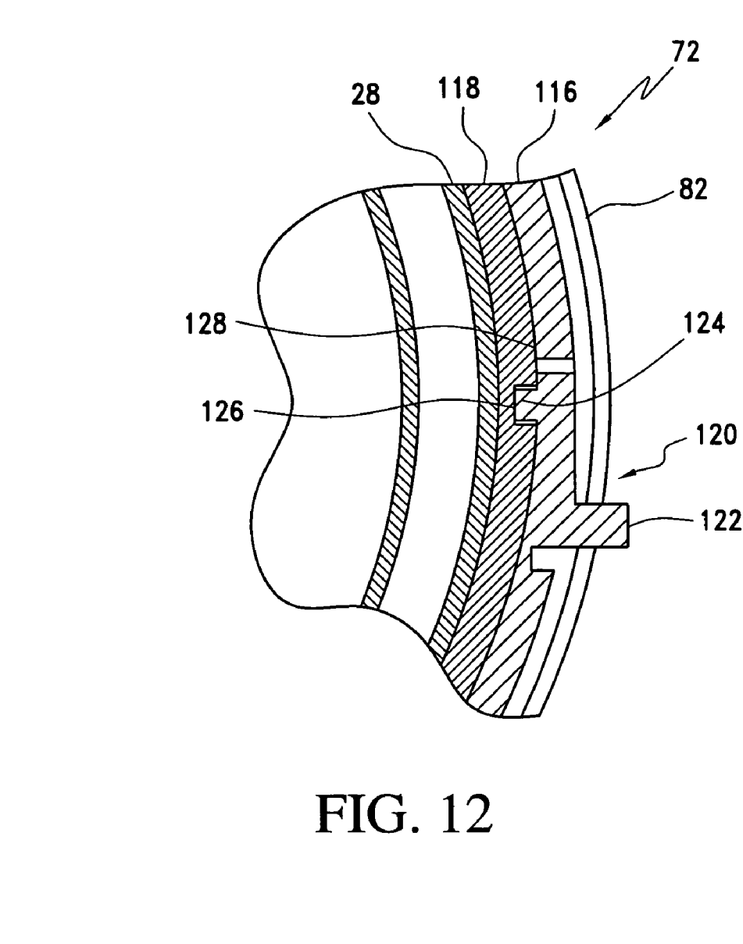
FIG. 12 is a cross sectional view along the line 12-12 in FIG. 7.
Figure 13:
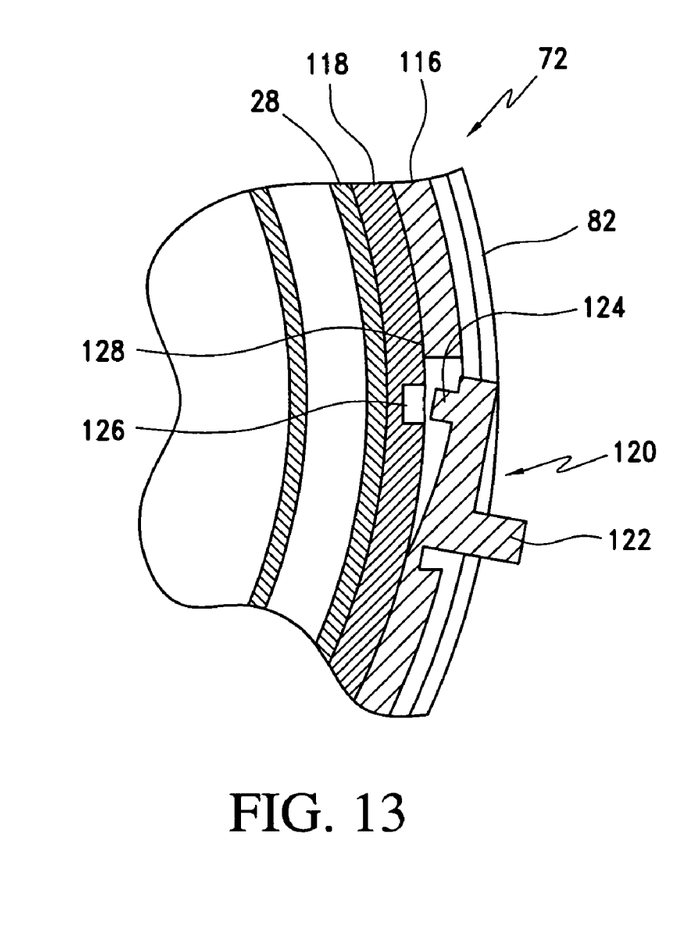
FIG. 13 is a cross sectional view along the line 13-13 in FIG. 8.

In accordance with the preferred embodiment, the iris seal 12 is composed of a rubber like member. The rubber like member is constructed in the shape of a cylindrical section with the upper and lower sections 88, 90 thereof having a wider diameter than the central section 92 (thereby offering a cross-section as shown in FIGS. 7 and 8). As will be appreciated based upon the following disclosure, the construction of the rubber like member creates a substantially planar iris seal 12 which is closed or opened when the upper seal ring 72 and the lower seal ring 28 are rotated relative to one another in opposite directions.

In accordance with a preferred embodiment, the rubber like member is formed from a thin film having a thickness of less than approximately 0.064 cm (0.025 inches) and made from a material having elasticity, such as, natural rubber, synthetic rubber, poly vinyl chloride, silicon and a variety of elastomers (for example, urethane, polyisoprene, silicone). As briefly mentioned above, the rubber like member is cylindrical and includes a central access opening 86 having a predetermined cross sectional area at the central section 92 thereof. The rubber like member is shaped such that the diameter of the opening decreases in the direction from the upper and lower sections 88, 90 to the central section 92 of the rubber like member. Furthermore, the upper and lower ends 74, 76 of the iris seal 12, which are fitted into the grooves 94, 96 of the upper seal ring 72 and the lower seal ring 28 and held therein with O-rings 98, 100, allow for detachment from the upper seal ring 72 and the lower seal ring 28. In accordance with a preferred embodiment, the O-rings 98, 100 are integrated into the iris seal 12, minimizing components and material cost. Because of such detachable structure of the rubber like member, it can be easily replaced by a fresh member when the used rubber like member is broken or worn. This technique would be useful for reusable devices.

Figure 5:
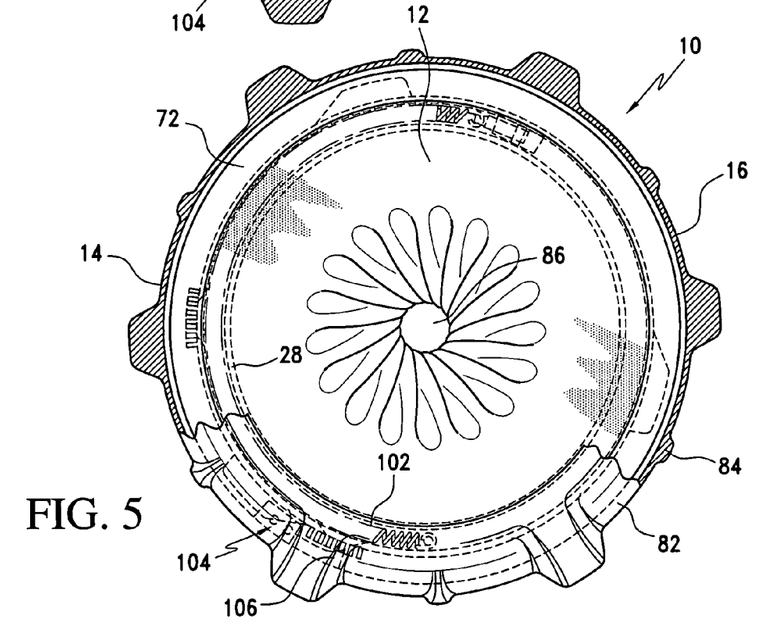
Figure 6:
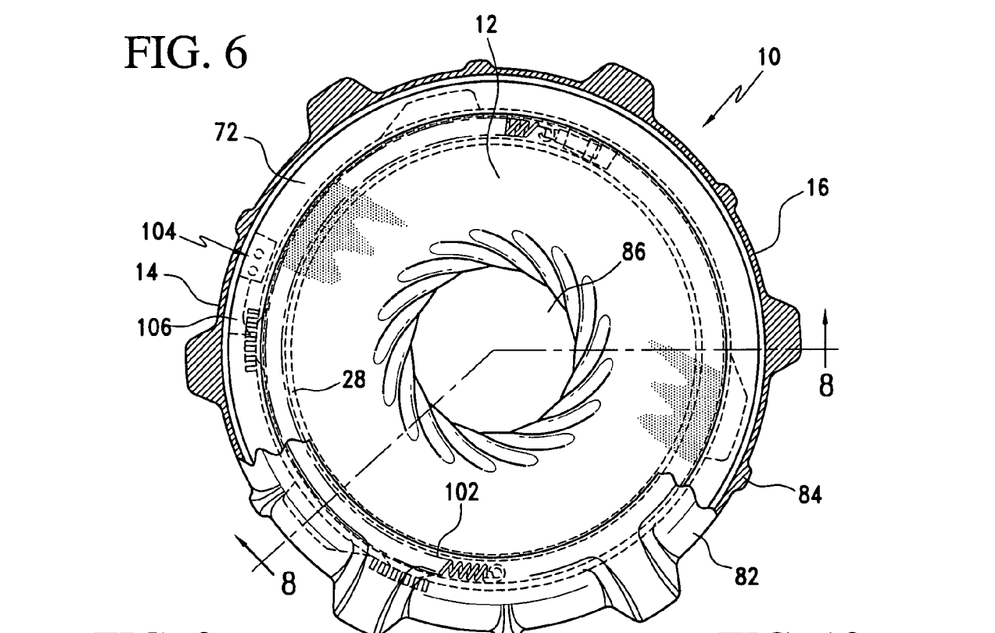

Referring to FIGS. 4, 5, 6, 7 and 8, a plan view and a sectional view are presented, showing the iris seal 12 in its respective closed and open states. FIGS. 6 and 8 show the iris seal 12 in a fully opened orientation for viewing within the cavity or insertion of an instrument or hand therethrough, while FIG. 5 shows a partially opened orientation sufficient for passing a hand therethrough when sealing thereabout is desired.

This open state is created when the upper seal ring 72 is rotated at a predetermined angle, for example, 15 degrees, from the closed state of the iris seal 12, and the access opening 86 is created.

In accordance with a preferred embodiment, the upper seal ring 72 is biased relative to the lower seal ring 28 by a spring 102. The spring 102 functions to return the iris seal 12 to its closed orientation after rotation of the upper seal ring 72 relative to the lower seal ring 28 to its open orientation. As such, the surgeon may rotate the upper seal ring 72 relative to the lower seal ring 28 through engagement of the contoured surface of the ergonomic cover member 82 or, by direct engagement with the iris seal 12 to move the iris seal 12 from its closed orientation to an open orientation opening the access opening 86 for passage of his or her hand therethrough. Once his or her hand is passed therethrough, the upper seal ring 72, ergonomic cover member 82 and/or the iris seal 12 are released allowing the action of the spring 102 to move the upper seal ring 72 and the iris seal 12 back toward the closed orientation.

As some surgeons may want to maintain an open position using the autoclosing device, a ratchet rotational control mechanism 104 has been developed wherein the surgeon has control over the spring biased action moving the upper seal ring 72 relative to the lower seal ring 28 and iris seal 12 from its open orientation to its closed orientation. Although a ratchet system is disclosed in accordance with a preferred embodiment of the present invention, those skilled in the art will appreciate that a seal assembly without a ratchet assembly could also be practiced within the spirit of the present invention.

In accordance with a preferred embodiment, and with reference to FIGS. 3 to 13, the upper seal ring 72 is seated within the track 70 of the lower seal ring 28 with the spring 102 biasing the upper seal ring 72 relative to the lower seal ring 28 for movement relative thereto opening the access opening 86. However, a ratchet rotational control mechanism 104 is positioned between the upper seal ring 72 and the lower seal ring 28. The ratchet rotational control mechanism 104 includes a ratchet arm 106 secured to the upper seal ring 72 which is oriented to engage upwardly facing first and second ratchet surfaces 108a, 108b composed of a plurality of ratchet teeth 109a, 109b on the lower seal ring 28 which functions to hold the upper seal ring 72 relative to the lower seal ring 28 as it is moved to an open orientation. In practice, the ratchet arm 106 is shaped and dimensioned to engage the teeth 109a, 109b of the ratchet surfaces 108a, 108b when rotated in a first direction (for example, and in accordance with a preferred embodiment, clockwise rotation when viewed from above). However, once the upper seal ring 72 is rotated such that the ratchet arm 106 moves beyond the rear ends 110a, 110b of the ratchet surfaces 108a, 108b, the ratchet arm 106 is free to move past the ratchet surfaces 108a, 108b as the upper seal ring 72 is rotated in a second direction opposite the first direction.

This is achieved by providing the ratchet arm 106 with a tapered distal end 112 which is biased by similar tapered surfaces 114a, 114b on the respective rear ends 110a, 110b of the ratchet surfaces 108a, 108b to ride under the ratchet surfaces 108a, 108b as the upper seal ring 72 is rotated relative to the lower seal ring 28 in a second direction. However, when the upper seal ring 72 is rotated in a first direction, the distal end 112 of the ratchet arm 106 is biased to ride over the upper surface of the ratchet surfaces 108a, 108b such that it engages the various teeth 109a, 109b to control movement of the upper seal ring 72 relative to the lower seal ring 28.

In accordance with a preferred embodiment of the present invention, first and second ratchet surfaces 108a, 108b are provided. The first ratchet surface 108a engages the ratchet arm 106 when the upper and lower seal rings 72, 28 are oriented to provide a relatively small opening in the iris seal 12 through which a medical practitioner may pass his or her hand to gain access to a body cavity. The configuration is especially suited to single hand interactions where a user may rotate the upper seal ring 72 relative to the lower seal ring 28 with the same hand which is to be passed through the present seal assembly 10. In particular, and as a result of the ratchet rotational control mechanism 104, a user may, for example, use his or her left hand to rotate the upper seal ring 72 relative to the lower seal ring 28 in a manner slightly or partially opening the iris seal 12 as shown in FIG. 5. When in this position, the audible click sound and slight resistance produced as the ratchet arm 106 moves over the first ratchet surface 108a will provide the user with an indication a stopping position has been reached. At this point, the user may release the upper seal ring 72 without fear that the iris seal 12 will snap back to its closed orientation. Rather, the ratchet rotational control mechanism 104 holds the upper and lower seal rings 72, 28 relative to each other, allowing the user to slip his or her hand through the opening in the iris seal 12. As the user pushes his or her hand through the iris seal 12, the outward force causes a slight rotation of the upper seal ring 72 relative to the lower seal ring 28 in a manner disengaging the ratchet arm 106 from the first ratchet surface 108a, and allowing the upper seal ring 72 to rotate relative to the lower seal ring 28 under the bias of the spring 102 to move the iris seal 12 back to its closed orientation, securely wrapping it about the user's wrist/forearm. As such, when the user pulls his or her arm from the seal assembly 10, the iris seal 12 will automatically close sealing the body cavity from the external environment.

The second ratchet surface 108b allows the seal assembly 10 to be locked with the central access opening 86 in a larger open configuration allowing for more complete access to the body cavity. As those skilled in the art will certainly appreciate, it is at times desirable to provide a large access opening to the body cavity. As such, the present seal assembly 10 is provided with a second ratchet surface 108b providing for locking of the upper seal ring 72 and the lower seal ring 28 relative to each other when the iris seal 12 is more fully opened as shown in FIG. 6.

As with the first ratchet surface 108a, the second ratchet surface 78b engages the ratchet arm 106 when the upper and lower seal rings 72, 28 are oriented in a particular orientation providing, in this case, a relatively large opening in the iris seal 12. A user rotates the upper seal ring 72 relative to the lower seal ring 28 to create an opening in the iris seal 12 beyond the small opening as shown in FIG. 5. Once the first ratchet surface 108a is passed (as indicated by the first series of audible clicks), the audible clicking sound produced as the ratchet arm 106 moves over the second ratchet surface 108b will provide the user with an indication a stopping position has been reached. At this point, the user may release the upper seal ring 72 without fear that the iris seal 12 will close, and proceed to utilize the large opening for access to the body cavity in a desired manner. When the user no longer requires this access, he or she may simply rotate the upper seal ring 72 relative to the lower seal ring 28 in a first direction slightly opening the iris seal 12, at which point the ratchet arm 106 will disengage from the second ratchet surface 108b and allow the upper seal ring 72 to rotate relative to the lower seal ring 28 under the bias of the spring 102 to move the iris seal 12 back to its closed orientation.

As mentioned above, a ratchet rotational control mechanism 104 is employed to control the relative position of the upper and lower seal rings 72, 28. As discussed above with reference to FIGS. 9, 10 and 11, this ratchet rotational control mechanism 104, however, requires that the upper seal ring 72 be moved beyond a specific release point before it will permit movement of the upper seal ring 72 relative to the lower seal ring 28 in a manner closing the access opening 86 under the forced supplied by the spring 102.

With this is mind, the upper seal ring 72 is provided with first and second ring members 116, 118 selectively connected via a latching mechanism 120 that controls rotational movement of the first ring member 116 relative to the second ring member 118. The first ring member 116 is substantially annular and provides the support structure for the ergonomic cover member 82 and the upper section 88 of the iris seal 12. The second ring member 118 is also substantially annular and is positioned adjacent the first ring member 116 for rotational movement relative thereto. In fact, the second ring member 118 is positioned between the first ring member 116 and the lower seal ring 28. As a result, the second ring member sits within the track 70 of the lower seal ring 28 and includes the components of the upper seal ring 72 permitting operation of the ratchet rotational control mechanism 104 described above. That is, the ratchet arm 106 is secured to, and extends from, the bottom of the second ring member 118. As such, movement of the second ring member 118 relative to the lower seal ring 28 is controlled by the ratchet rotational control mechanism 104.

As briefly discussed above, a latch mechanism 120 links the first ring member 116 and the second ring member 118. As a result, the first ring member 116 and the second ring member 118 may move in unison when the latch mechanism 120 is in its locked orientation coupling the first ring member 116 to the second ring member 118. Similarly, the first ring member 116 and the second ring member 118 may move freely relative to each other when the latch mechanism 120 is in it unlocked orientation. As a result, when the latch mechanism 120 is in its unlocked orientation, the first ring member 116, to which the upper section 88 of the iris seal 12 is coupled, is free to rotate without the ratchet rotational control mechanism 104 controlling the movement relative thereto.

The latch mechanism 120 includes a pivotally mounted latch 122 coupled to the first ring member 116. The latch 122 is designed to selectively engage the second ring member 118 for permitting or preventing rotation of the first ring member 116 relative to the second ring member 118. More particularly, the latch 122 includes an inwardly directed projection member 124 shaped and dimensioned for seating within a recess 126 formed along an outer surface 128 of the second ring member 118. As such, when the inwardly directed projection member 124 is seated within the recess 126 of the second ring member 118, the first ring member 116 is coupled to the second ring member 118 and must move in unison therewith such that the first ring member 116 is under the control of the ratchet rotational control mechanism 104. However, when the latch 122 is pivoted such that the inwardly directed projection member 124 is moved from the recess 126 of the second ring member 118, the first ring member 116 is once again free to rotate relative to the second ring member 118 allowing one to open and close the iris seal 12 as the operator sees fit. In practice, such a mechanism allows for quick release of the iris seal 12 without the need for twisting of the upper seal ring 72 relative to the lower seal ring 28 against the bias of the ratchet rotational control mechanism 104.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A seal assembly for permitting hand assisted laparoscopic procedures, comprising:
   a seal cap including a seal positioned within a housing, the housing including a lower seal ring having a track which supports an upper seal ring for relative rotational motion, wherein the seal includes an upper end coupled to the upper seal ring and a lower end coupled to the lower seal ring wherein the seal is supported between the upper seal ring and the lower seal ring for rotation between an open orientation and a closed orientation;
   the upper seal ring including a first ring member to which the upper end of the seal is directly coupled and a second ring member oriented for movement relative thereto, wherein a latching mechanism is positioned between the first ring member and the second ring member for selectively controlling movement of the first ring member relative to the second ring member by moving between a locked orientation where the first ring member and the second ring member move in unison and an unlocked orientation where the first ring member and the second ring member may move freely relative to each other;
   a rotational control mechanism controlling motion of the upper seal ring relative to the lower seal ring;
   wherein when the latch mechanism is in its unlocked orientation, the first ring member, to which the upper end of the iris seal is coupled, is free to rotate without the rotational control mechanism controlling movement of the first ring member relative to the lower seal ring.

2. The seal assembly according to claim 1, wherein the rotational control mechanism is positioned between the second ring member and the lower seal ring.

3. The seal assembly according to claim 1, wherein the rotational control mechanism is a ratchet rotational control mechanism.

4. The seal assembly according to claim 3, wherein the rotational control mechanism is positioned between the second ring member and the lower seal ring.

5. The seal assembly according to claim 3, wherein the ratchet rotational control mechanism includes a ratchet arm oriented to engage a ratchet surface.

6. The seal assembly according to claim 5, wherein the ratchet arm is coupled to the upper seal ring and the ratchet surface is coupled to the lower seal ring.

7. The seal assembly according to claim 6, wherein the ratchet arm is coupled to the second ring member of the upper seal ring.

8. The seal assembly according to claim 6, further including first and second ratchet surfaces on the lower seal ring.

9. The seal assembly according to claim 1, wherein the seal is an iris seal.

10. The seal assembly according to claim 1, further including a spring biasing the upper seal ring relative to the lower seal ring.

11. The seal assembly according to claim 1, wherein an upper end of the seal is connected to the upper seal ring and a lower end of the seal is connected to the lower seal ring.

12. The seal assembly according to claim 1, further including an ergonomic cover member secured to the upper seal ring, wherein the ergonomic cover member includes a contoured outer surface providing for improved handling and twisting of the upper seal ring for opening and closing the seal.

13. A seal assembly for permitting hand assisted laparoscopic procedures, comprising:
   a seal cap including a seal positioned within a housing, the housing including a lower seal ring having a track which supports an upper seal ring for relative rotational motion, wherein the seal includes an upper end coupled to the upper seal ring and a lower end coupled to the lower seal ring wherein the seal is supported between the upper seal ring and the lower seal ring for rotation between an open orientation and a closed orientation;
   the upper seal ring including a first ring member to which the upper end of the seal is directly coupled and a second ring member oriented for movement relative thereto, wherein a latching mechanism is positioned between the first ring member and the second ring member for selectively controlling movement of the first ring member relative to the second ring member by moving between a locked orientation where the first ring member and the second ring member move in unison and an unlocked orientation where the first ring member and the second ring member may move freely relative to each other;
   a ratchet arm and a ratchet surface positioned between the lower seal ring and the second ring member, the ratchet arm being oriented to engage the ratchet surface to control motion of the upper seal ring relative to the lower seal ring;
   wherein when the latch mechanism is in its unlocked orientation, the first ring member, to which the upper end of the iris seal is coupled, is free to rotate without the ratchet arm and the ratchet surface controlling movement of the first ring member relative to the lower seal ring.

14. The seal assembly according to claim 13, wherein the ratchet arm is coupled to the upper seal ring and the ratchet surface is coupled to the lower seal ring.

15. The seal assembly according to claim 14, wherein the ratchet arm is coupled to the second ring member of the upper seal ring.

16. The seal assembly according to claim 14, further including first and second ratchet surfaces on the lower seal ring.

17. The seal assembly according to claim 13, wherein the seal is an iris seal.

18. The seal assembly according to claim 13, further including a spring biasing the upper seal ring relative to the lower seal ring.

19. The seal assembly according to claim 13, wherein an upper end of the seal is connected to the upper seal ring and a lower end of the seal is connected to the lower seal ring.

20. The seal assembly according to claim 13, further including an ergonomic cover member secured to the upper seal ring, wherein the ergonomic cover member includes a contoured outer surface providing for improved handling and twisting of the upper seal ring for opening and closing the seal.

* * * * *